(12) United States Patent
Limon

(10) Patent No.: US 12,295,659 B2
(45) Date of Patent: May 13, 2025

(54) SUBJECTIVE REFRACTION EXAM SYSTEM

(71) Applicant: 6OVER6 VISION Ltd., Tel Aviv (IL)

(72) Inventor: Ofer Limon, Tel Aviv (IL)

(73) Assignee: 6OVER6 VISION LTD., Tel Aviv (IL)

( * ) Notice: Subject to any disclaimer, the term of this patent is extended or adjusted under 35 U.S.C. 154(b) by 831 days.

(21) Appl. No.: 17/361,095

(22) Filed: Jun. 28, 2021

(65) Prior Publication Data

US 2021/0401282 A1 Dec. 30, 2021

Related U.S. Application Data

(60) Provisional application No. 63/044,910, filed on Jun. 26, 2020.

(51) Int. Cl.
*A61B 3/032* (2006.01)
*A61B 3/00* (2006.01)

(52) U.S. Cl.
CPC ............ *A61B 3/032* (2013.01); *A61B 3/0025* (2013.01); *A61B 3/0058* (2013.01)

(58) Field of Classification Search
CPC ..... A61B 3/0025; A61B 3/032; A61B 3/0058; A61B 3/14; A61B 3/0033; A61B 2017/00221; A61B 2090/3616; A61B 2090/502; A61B 3/00; A61B 3/0008; A61B 3/0083; A61B 3/024; A61B 3/102; A61B 3/135; A61B 5/0066; A61B 5/0073; A61B 90/361; A61B 2090/371; A61B 2090/372; A61B 3/0041; A61B 3/02; A61B 3/028; A61B 3/036; A61B 3/18; A61B 34/35; H04N 13/239; H04N 23/631; H04N 13/00; H04N 13/344; H04N 23/50; H04N 23/56; H04N 23/661; H04N 23/74; H04N 5/2625; H04N 7/15; H04N 7/181; H04N 7/183; H04N 1/603; H04N 1/6086; H04N 1/6088; H04N 13/161; H04N 13/178; H04N 13/189; H04N 13/305; H04N 13/359; H04N 19/107; H04N 19/23; H04N 19/61;
(Continued)

(56) References Cited

U.S. PATENT DOCUMENTS 6,072,443 A 6/2000 Nasserbakht et al.
6,386,707 B1 5/2002 Pellicano
(Continued)

FOREIGN PATENT DOCUMENTS

ES 2652164 * 1/2018 ............ A61B 3/111
JP H06237895 A 8/1994
(Continued)

OTHER PUBLICATIONS

International Search Report and Written Opinion for PCT/IB2021/000447 dated Nov. 24, 2021 (14 pages).
Extended European Search Report dated May 10, 2024 (8 pages).

*Primary Examiner* — Brandi N Thomas
(74) *Attorney, Agent, or Firm* — Dorsey & Whitney LLP

(57) ABSTRACT

Methods and systems herein can include displaying at least one image to a test subject, wherein the at least one image has a visual appearance to the test subject based on physical characteristics of the eyes of the test subject, obtaining input from the test subject regarding the visual appearance of the at least one image, and calculating an optical parameter of the test subject based on the input from the test subject.

17 Claims, 28 Drawing Sheets

(58) Field of Classification Search
CPC ............. H04N 2007/145; H04N 23/45; H04N 23/531; H04N 7/14; H04N 7/147; H04N 7/18

See application file for complete search history.

(56) References Cited

U.S. PATENT DOCUMENTS

| | | | |
|---|---|---|---|
| 2008/0309880 A1* | 12/2008 | Fisher | A61B 3/032 |
| | | | 351/239 |
| 2009/0109398 A1* | 4/2009 | Ellenbogen | A61H 5/00 |
| | | | 351/203 |
| 2010/0265463 A1 | 10/2010 | Lai | |
| 2012/0212598 A1 | 8/2012 | Mowrey et al. | |
| 2012/0212706 A1 | 8/2012 | Chou et al. | |
| 2016/0317025 A1* | 11/2016 | Lee | A61B 5/0022 |
| 2019/0175011 A1 | 6/2019 | Jensen et al. | |
| 2019/0307324 A1 | 10/2019 | Limon | |
| 2020/0129060 A1* | 4/2020 | Lee | A61B 3/18 |

FOREIGN PATENT DOCUMENTS

| | | |
|---|---|---|
| JP | 2016520336 A | 7/2016 |
| JP | 2018143554 A | 9/2018 |
| RU | 2210972 C1 | 8/2003 |
| WO | 200434893 A1 | 4/2004 |
| WO | 2011133945 A1 | 10/2011 |

\* cited by examiner

FIG. 7

Example of Shapes step for a user with a right eye sphere of -3D, cylinder of -0.5D, and axis of 135 degrees.

| Step and Block | User Sees | User Hears | User's Actions |
|---|---|---|---|
| Shapes - screening block (Gauge) | | Move back until the you are in the right position. | User moves back 60 cm from the mobile device |
| Shapes - screening | | How many ducks do you see? | User's answer: 1 |
| Shapes - Approximate sphere rough | | There are shapes on the screen, only some of them are ducks. Move slowly closer to the phone until you first see the ducks. | User moves toward the mobile device and stands still |
| Shapes - Approximate sphere rough | | Hold still. How many sharp ducks to you see? | User's answer: 1 |

FIG. 9A

Example of SNR step for a user with a right eye sphere of -3D, cylinder of -0.5D, and axis of 135 degrees.

| Step and Block | User Sees | User Hears | User's Actions |
|---|---|---|---|
| SNR flow | | Are some of the lines darker than others? Answer yes or no. | User's answer: Yes |
| SNR Axis measurement - rough block | | What color does the darkest line point to? Answer the name of the color. | User's answer: Blue |
| SNR Axis measurement - fine block | | Great! What colors do the darkest lines point to? You may pick more than one. | User's answer: White, green, red |
| SNR Axis measurement - fine block | | Would you like to change your selection? Say yes or no. | User's answer: No |
| SNR how sharp #1 | | Focus on the lines pointing to the red dots: From 1 to 5, how sharp is the darkest line? 1 is blurred; 5 is very sharp. | User's answer: 5 |

Continued →

FIG. 9B
| Step and Block | User Sees | User Hears | User's Actions |
|---|---|---|---|
| SNR flow (Gauge) | 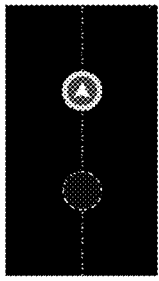 | N/A | User moves 0.5D further away from the mobile device |
| SNR how sharp #3 | 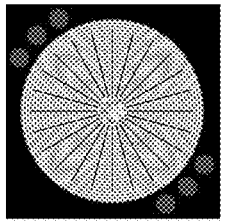 | From 1 to 5, how sharp is the blackest line? | User's answer: 3 |
| SNR how sharp #5 | 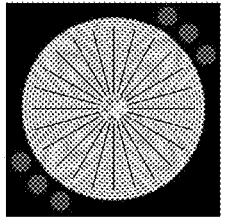 | Focus on the lines pointing to the red dots. From 0 to 5, how sharp is the darkest line? 0 is very blurred; 5 is very sharp. | User's answer: 1 |

FIG. 11A

Example of Achromatic MonoGrill step for a user with a right eye sphere of -3D, cylinder of -0.5D, and axis of 135 degrees.

| Step and Block | User Sees | User Hears | User's Actions |
|---|---|---|---|
| G Series (Gauge) | | N/A | User moves closer to the mobile device. |
| G Series - Training | | In the next step there are two thin, lighter lines over a black rectangle. If you see the two lines say "Yes;" if you don't, say "No;" if you are not sure, say "Next." | User's answer: Yes |
| G Series - Training | | And now? | User's answer: No |
| G Series - Training | | And now? | User's answer: Yes |

Continued →

FIG. 11B
| G Series - Training | 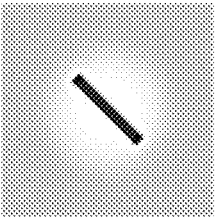 | And now? | User's answer: No |
|---|---|---|---|
| G Series - Training | 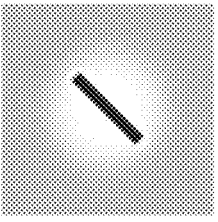 | And now? | User's answer: No |
| G Series - Sphere - distance validation block | 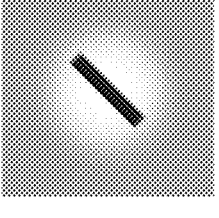  Target size = 0.65 LogMAR | Do you see the two light lines? | User's answer: Yes |
| G Series - Sphere - distance validation block | 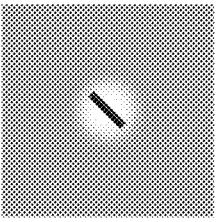  Target size = 0.35 LogMAR | (beep beep) | User's answer: No |
Continued ➔

FIG. 11C

| G Series - Sphere - distance validation block | 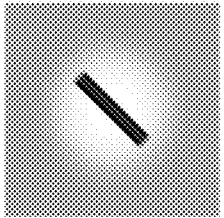<br>Target size = 0.65 LogMAR | (beep beep) | User's answer: Yes |
|---|---|---|---|
| G Series - Sphere - distance validation block | 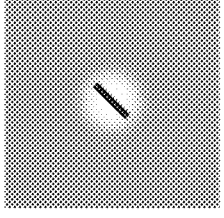<br>Target size = 0.35 LogMAR | (beep beep) | User's answer: No |
| G Series - Sphere - Series block | 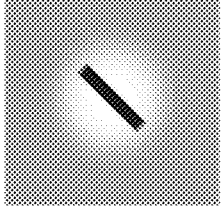<br>Target size = 0.6 LogMAR | And now? | User's answer: Yes |
| G Series - Sphere - Series block | 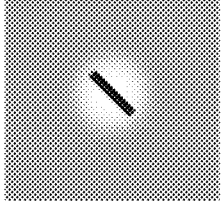<br>Target size = 0.45 LogMAR | (beep beep) | User's answer: Next |

Continued →

*FIG. 11D*
| G Series - Sphere - Series block | 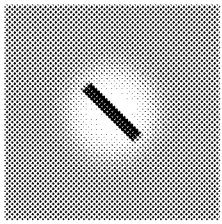<br>Target size = 0.55 LogMAR | (beep beep) | User's answer: Yes |
|---|---|---|---|
| G Series - Sphere - Series block | 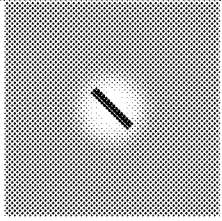<br>Target size = 0.40 LogMAR | (beep beep) | User's answer: No |
| G Series - Sphere - Series block | 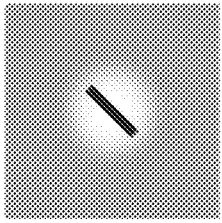<br>Target size = 0.50 LogMAR | (beep beep) | User's answer: Yes |
| G Series - Cyl (Gauge) | 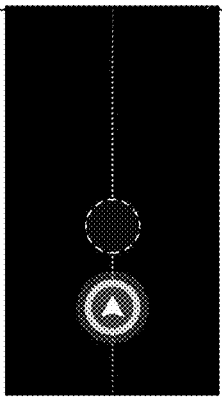 | | User moves to calculated sphere (closer to the mobile device) |
Continued ➔

FIG. 11E

| G Series - Cyl -distance validation block | 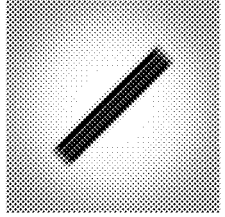<br>Target size = 0.85 LogMAR | And now? | User's answer: Yes |
|---|---|---|---|
| G Series - Cyl -distance validation block | 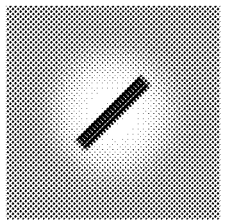<br>Target size = 0.65 LogMAR | (beep beep) | User's answer: No |
| G Series - Cyl -distance validation block | 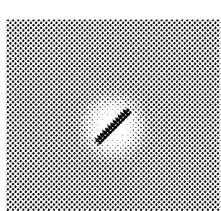<br>Target size = 0.35 LogMAR | (beep beep) | User's answer: No |
| G Series - Cyl -distance validation block | 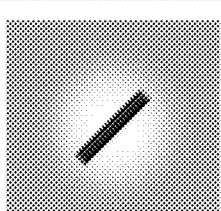<br>Target size = 0.65 LogMAR | (beep beep) | User's answer: No |

Continued ➔

FIG. 11F
| G Series - Cyl -distance validation block | 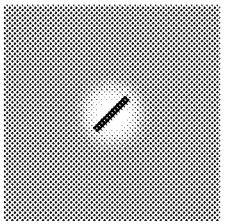<br>Target size = 0.35 LogMAR | (beep beep) | User's answer: Yes |
|---|---|---|---|
| G Series - CYL - Series block | 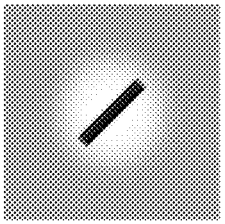<br>Target size = 0.6 LogMAR | And now? | User's answer: Yes |
| G Series - CYL - Series block | 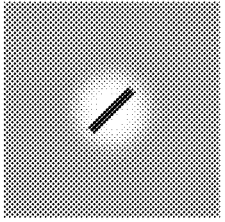<br>Target size = 0.45 LogMAR | (beep beep) | User's answer: No |
| G Series - CYL - Series block | 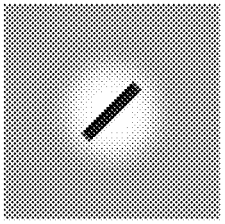<br>Target size = 0.55 LogMAR | (beep beep) | User's answer: Yes |
Continued →

FIG. 11G
| G Series - CYL - Series block | 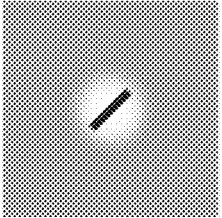 Target size = 0.40 LogMAR | (beep beep) | User's answer: No |
|---|---|---|---|
| G Series - CYL - Series block | 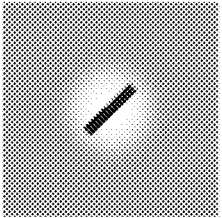 Target size = 0.50 LogMAR | (beep beep) | User's answer: Next |

FIG. 13
Example of Achromatic MonoGrill step for a user with a right eye sphere of -3D, cylinder of -0.5D, and axis of 135 degrees.
| Step and Block | User Sees | User Hears | User's Actions |
|---|---|---|---|
| Low CYL validation - Gauge | 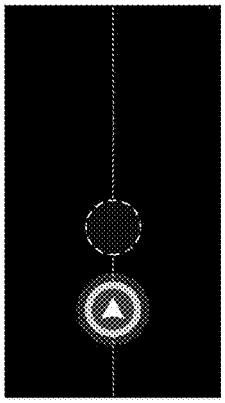 | N/A | User moves away to final sphere. |
| Low CYL validation | 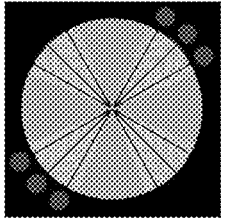 | Focus on the lines pointing to the red dots. From 0 to 5, how sharp is the darkest line? 0 is very blurred; 5 is very sharp. | User's answer: 3 |

FIG. 14

Example of Axis Refinement step for a user with a right eye sphere of -3D, cylinder of 1.5D, and axis of 5 degrees.

| Step and Block | User Sees | User Hears | User's Actions |
|---|---|---|---|
| SNR Axis measurement - fine block | 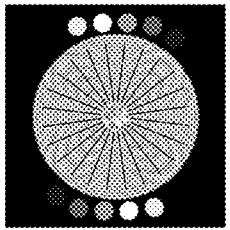 | What colors do the darkest lines point to? You may pick more than one | User's answer: White, green |
| SNR Axis measurement - fine block | 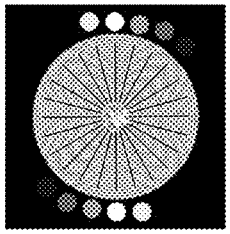<br>Target is rotated 7.5 degrees | What colors do the darkest lines point to? You may pick more than one. | User's answer: White, green |

FIG. 15A

Example of Accommodation Control step for a user with a right eye sphere of -3D, cylinder of -0.5D, and axis of 135 degrees.

| Step and Block | User Sees | User Hears | User's Action |
|---|---|---|---|
| Accommodation control | 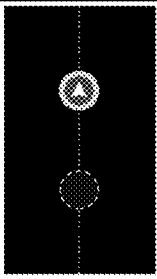 | N/A | User moves to lowest sphere +0.25D. |
| Accommodation control | "Uncover your eyes." (3 sec internal countdown) | Now, uncover your eye and look at the distance. | User removes hand covering eye and looks to the distance. |
| Accommodation control | "Cover your right eye." | N/A | User covers his right eye. |
| Accommodation control | 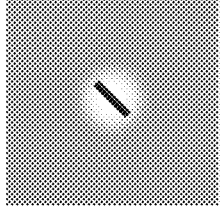<br>Target size = 0.35 LogMAR | N/A | User's answer: "Yes" within 4 sec. |
| Accommodation control | 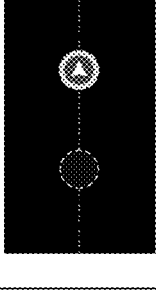 | N/A | User moves 0.25D away from the mobile device. |

| Step and Block | User Sees | User Hears | User's Action |
|---|---|---|---|
| Accommodation control | "Uncover your eye and look to the distance." | Now, uncover your eye and look to the distance. | User removes hand covering eye and looks to the distance. |
| Accommodation control | "Cover your left eye." | Cover your left eye. | User covers his left eye. |
| Accommodation control | 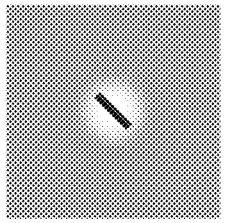 Target size = 0.35 LogMAR | N/A | User's answer: "No" within 4 sec |

FIG. 16

Example of VA step for a user with a right eye sphere of -3D, cylinder of -0.5D, and axis of 135 degrees.

| Step and Block | User Sees | User Hears | User's Actions |
|---|---|---|---|
| VA | 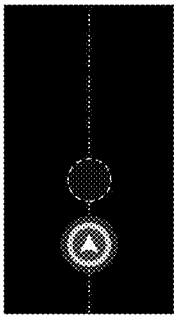 | N/A | User moves to final sphere. |
| VA | 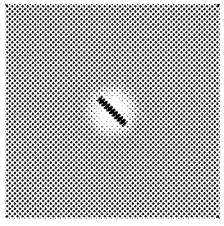<br>Target size = 0.25 LogMAR | In the next step, there are two thin, lighter lines over a black rectangle. If you see the two lines say "Yes;" if you don't say "No;" if you are not sure, say "Next." | User's answer: No |
| VA | 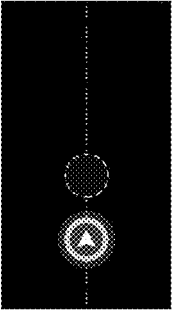 | N/A | User moves -0.25D towards the phone. |
| VA | 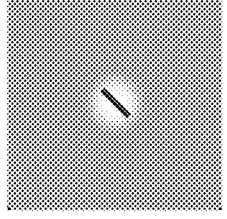<br>Target size = 0.25 LogMAR | Do you see the two light lines? | User's answer: Yes |

FIG. 18A

Example of CYL Magnitude step for a user with a right eye sphere of -3D, cylinder of -0.5D, and axis of 135 degrees.

| Step and Block | User Sees | User Hears | User's Actions |
| --- | --- | --- | --- |
| CYL Magnitude | | N/A | User moves 0.25D away from the mobile device. |
| CYL Magnitude | | In the next step, there are two targets. Where do you see two distinct lines? Answer "A," "B," "Both," or "None." | User's answer: A |
| CYL Magnitude | Target B size = 0.1 LogMAR | N/A | User's answer: None |
| CYL Magnitude | | Move forward until you are in the right position. | User moves 0.25D closer to the mobile device. |

| CYL Magnitude | | And now, where do you see two distinct lines? Answer "A," "B," "Both," or "None." | User's answer: Both |
|---|---|---|---|
| CYL Magnitude | | Move back until you are in the right position. | User moves 0.25D away from the mobile device. |
| CYL Magnitude | | And now? | User's answer: None |

SUBJECTIVE REFRACTION EXAM SYSTEM

CROSS-REFERENCE TO RELATED APPLICATIONS

This claims priority to U.S. Patent Application No. 63/044,910, filed 26 Jun. 2020 and entitled, "SUBJECTIVE REFRACTION EXAM SYSTEM," the entire disclosure of which is hereby incorporated by reference.

TECHNICAL FIELD

The present disclosure generally relates to systems and methods for providing self-administered medical recommendations and specifically relates to self-administered subjective refraction exam systems for measuring refractive error in eyes.

BACKGROUND

A refraction, also called a vision test or an eye exam, is commonly given by an eye doctor to determine whether the patient needs (or needs changes to) prescription lenses such as eyeglasses and contact lenses. The doctor often presents images, symbols, or words to a patient who comments on the sharpness or blurriness of their vision, and that information is used to determine a prescription for the patient. In some cases, doctors may have equipment configured to scan or otherwise measure characteristics of the patient's lens and other eye structures to obtain a prescription. However, this means that prescriptions are difficult to obtain without the doctor's expertise and experience or without access to specialized equipment. For this and other reasons, there is a constant need for improvements in the field of refraction exam systems for measuring refractive error in eyes.

SUMMARY

One aspect of the disclosure relates to a method comprising displaying at least one image to a test subject, wherein the at least one image has a visual appearance to the test subject based on physical characteristics of an eye of the test subject, obtaining input from the test subject regarding the visual appearance of the at least one image, and transmitting the input from the test subject.

In some embodiments, displaying the at least one image to the test subject and obtaining input from the test subject includes: displaying a set of shapes to the test subject and obtaining input indicating sphere of the eye; displaying a set of spokes and rings to the test subject and obtaining input indicating a cylinder measurement of the eye; displaying an accommodation control image to the test subject and obtaining input validating the sphere of the eye; displaying a visual acuity test image and obtaining input a best corrected visual acuity (BCVA) of the eye; and providing instructions to relax the eye.

In some embodiments, displaying the at least one image includes displaying the at least one image at a first size and displaying the at least one image at a second size. The at least one image can be simultaneously or sequentially displayed at the first and second sizes.

Displaying the at least one image can include displaying the at least one image at a first distance measured along an optical path between the test subject and the at least one image and displaying the at least one image at a second distance measured along an optical path between the test subject and the at least one image.

In some embodiments, the input is a subjective input based on the physical characteristics of the eye of the test subject. The input from the test subject can include an indication of a brightness value of a portion of the at least one image. In some embodiments, the method further comprises providing instructions to the test subject to change a length of an optical path between the test subject at the at least one image. The input from the test subject can include an indication of sharpness of a portion of the at least one image.

Another aspect of the disclosure relates to a product comprising one or more tangible computer-readable, non-transitory storage media comprising computer-executable instructions operable to, when executed by at least one computer processor, enable the at least one computer processor to cause a computing device to: display at least one image to a test subject, wherein the at least one image has a visual appearance to the test subject based on physical characteristics of an eye of the test subject; obtain input from the test subject regarding the visual appearance of the at least one image; and transmit the input from the test subject.

Yet another aspect of the disclosure relates to an apparatus for subjectively testing an optical parameter of an eye of a test subject, with the apparatus comprising: a processor; a display; an input device; a network device; and a memory device including executable instructions. The instructions can be operable, when executed by the processor, to: display at least one image to a test subject via the display, wherein the at least one image has a visual appearance to the test subject based on physical characteristics of an eye of the test subject; obtain input from the test subject via the input device regarding the visual appearance of the at least one image; and transmit the input from the test subject via the network device.

The above summary of the present invention is not intended to describe each embodiment or every implementation of the present invention. The figures and the detailed description that follow more particularly exemplify one or more preferred embodiments.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

FIG. 7 shows an example group of steps for a shapes test.

FIGS. 9A-9B show an example group of steps for a spokes and rings test.

FIGS. 11A-11G show an example group of steps for an achromatic monogrill test.

FIG. 13 shows an example group of steps for a cylinder validation test.

FIG. 14 shows an example group of steps for an axis refinement test.

FIGS. 15A-15B show an example group of steps for an accommodation control test.

FIG. 16 shows an example group of steps for a visual acuity test.

FIGS. 18A-18B show an example group of steps for a cylinder magnitude test.

Figure 1:
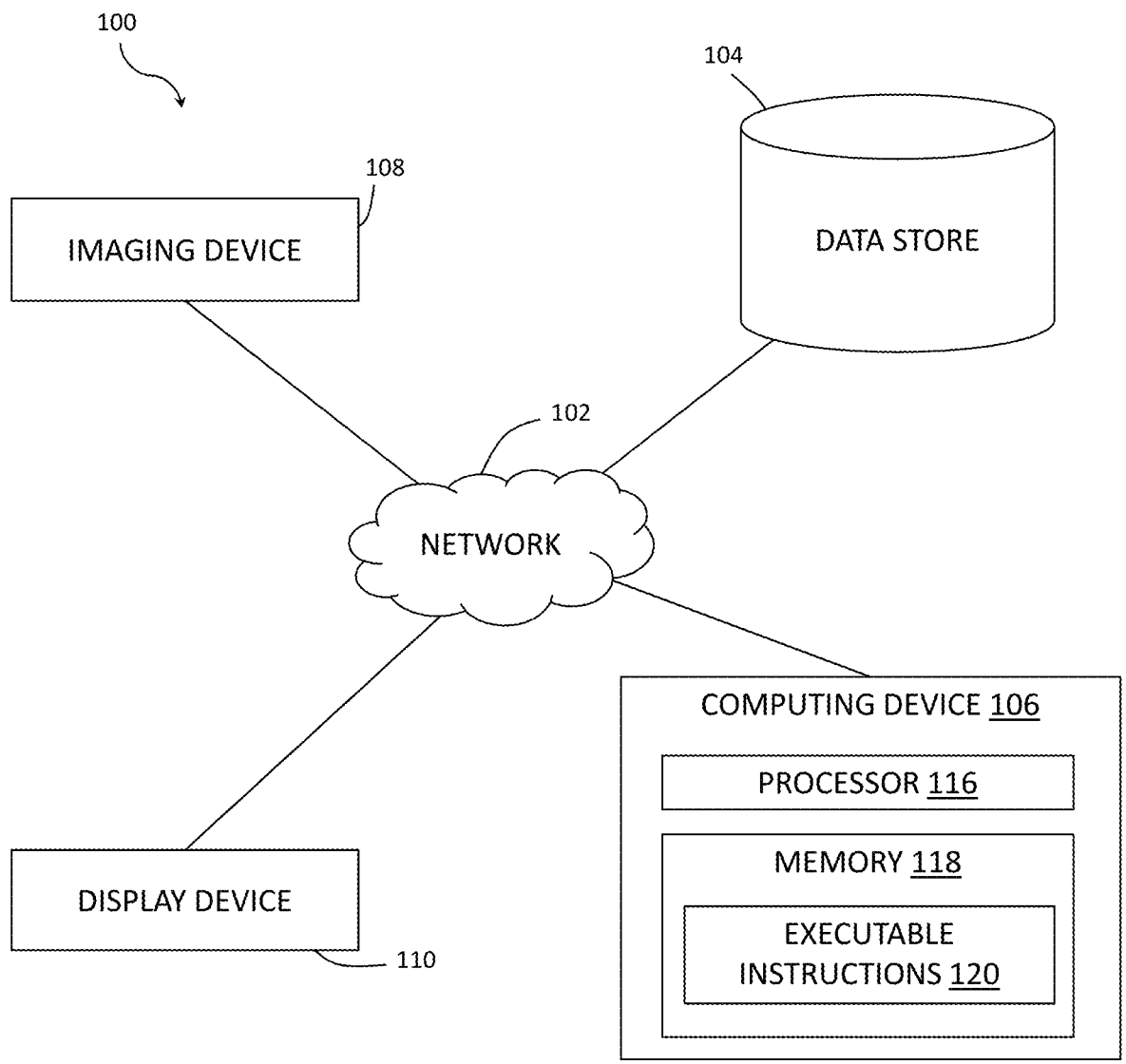
FIG. 1 is a schematic illustration of a system 100 for obtaining a subjective refraction of a test subject.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

Embodiments of the present disclosure relate to a subjective refraction test process comprising a combination of several stages or portions of the test process. Each of the stages can include displaying at least one specifically engineered image to a user (i.e., a test subject), which image or set of images may referred to as a "target." The target can have a different visual appearance to the subject according to the physical characteristics of their eyes (e.g., their refraction, color aptitude, etc.), their distance from the target, the size of the target, the graphic design of the target (e.g., contrast, brightness, etc.), and similar factors. In each stage, the test process can be used to determine one or more optical parameters of the subject based on measurements of and/or calculations of a distance along an optical path from the target to the test subject, based on changing the target size, and/or based on what the test subject is actually seeing based on their input (e.g., verbal responses or other data entry into a computing device). Taken together, these parameters can be used to determine details of the refraction error of the subject, including, for example, their spherical, cylindrical, and axial measurements. In some embodiments, the test process can include instructing the subject via visual and audio cues to guide the user through the exam. In some configurations, the exam is performed for each eye separately, while covering the opposite eye, so the test subject performs the test twice.

The test process can be self-administered, meaning the test subject can be the user operating and implementing the test process. In some embodiments, the test subject can therefore be alone or receive no assistance from other people while completing the test process. The results of the test process can, in some cases, be provided to a third party (e.g., an eyecare professional) to interpret the results and take appropriate clinical action. Information gathered using the test process (e.g., the test subject's spherical, cylindrical, and axial measurements) can be used to form a diagnosis of the subject's needs. For example, refractive error measurements of the test subject can be used to formulate a prescription for glasses and/or contact lenses for the test subject.

The test process can be used with test subjects of various ages, including, for example, male and female adults aged 18 to 39, and with test subjects of various glasses and/or contact lens prescriptions, including, for example, sphere power between 1.00 D to −5.00 D, cylinder power up to −2.50 D, and total power (sphere+cylinder) up to −6.00 D.

In some embodiments, measurements captured in the test process are not displayed to the user or test subject. They may instead be submitted to a third party, such as a licensed eyecare provider, for access and interpretation. Thus, in some cases, the third party can be enabled to access the output of the test process to take appropriate action (e.g., clinical action or validation). The third party can access the test process measurements and related information via a testing device used to obtain the measurements and related information, or the information can be transmitted to the third party (e.g., via a network) for their access.

Various types of outputs can be generated using the above-indicated processes and systems, including, for example, information about concordance of output (including sphere power, cylinder power, and cylinder axis for both eyes) for each eye by performing two separate test processes or information about concordance of binocular BCVA between the test process and SOC assessments performed in succession. Furthermore, information about concordance of output (including sphere power, cylinder power, and cylinder axis for both eyes) for each eye between the test process and SOC assessments performed successively can be generated.

In an example embodiment, information about concordance for each measurement in each eye can indicate whether 80 percent are within the certain optical parameters, such as, for example, sphere power: ±0.50 D, cylinder power: ±0.50 D, and cylinder axis: ±20 degrees. In some embodiments, the axis parameter may not be compared when cylinder power is between −0.25 D and 0.00 D.

The present description provides examples, and is not limiting of the scope, applicability, or configuration set forth in the claims. Thus, it will be understood that changes may be made in the function and arrangement of elements discussed without departing from the spirit and scope of the disclosure, and various embodiments may omit, substitute, or add other procedures or components as appropriate. For instance, the methods described may be performed in an order different from that described, and various steps may be added, omitted, or combined. Also, features described with respect to certain embodiments may be combined in other embodiments.

FIG. 1 is a schematic illustration of a system 100 for obtaining a subjective refraction of a test subject in accordance with examples described herein. It should be understood that this and other arrangements and elements (e.g., machines, interfaces, function, orders, and groupings of functions, etc.) can be used in addition to or instead of those shown, and some elements may be omitted altogether. Further, many of the elements described may be implemented as discrete or distributed components or in conjunction with other components, and in any suitable combination and location. Various functions described herein as being performed by one or more components may be carried out by firmware, hardware, and/or software. For instance, and as described herein, various functions may be carried out by a processor executing instructions stored in memory.

Among other components not shown, system 100 of FIG. 1 includes at least one data store 104, at least one computing device 106, at least one imaging device 108, and at least one display device 110. Computing device 106 can include processor 116 and memory 118. Memory 118 includes (e.g., may be encoded with) executable instructions 120 for performing a subjective refraction test process. The memory 118 can comprise a non-transitory computer-readable medium having instructions 120 stored therein or encoded thereon. The imaging device 108 can capture an image (e.g., photograph) or series of images (e.g., photographs or videos). It should be understood that system 100 shown in FIG. 1 is an example of one suitable architecture for implementing certain aspects of the present disclosure. Additional, fewer, and/or different components may be used in other examples. It should be noted that implementations of the present disclosure are equally applicable to other types of devices such as mobile computing devices and devices accepting gesture, touch, and/or voice input. Any and all such variations, and any combination thereof, are contemplated to be within the scope of implementations of the present disclosure. Further, although illustrated as separate components of computing device 106, any number of components can be used to perform the functionality described herein. Although illustrated as being a part of computing device 106, the components can be distributed via any number of devices. For example, processor 116 can be provided via one device, sever, or cluster of servers, while memory 118 may be provided via another device, server, or cluster of servers.

As shown in FIG. 1, computing device 106, imaging device 108, and display device 110 may electronically communicate with each other via network 102, which may include, without limitation, one or more direct (e.g., wired) connections, local area networks (LANs), and/or wide-area networks (WANs). Such networking environments are commonplace in offices, enterprise-wide computer networks, laboratories, homes, intranets, and the Internet. Accordingly, network 102 is not further described herein. It should be understood that any number of computing devices, sensors, and/or meters may be employed within system 100 within the scope of implementations of the present disclosure. Each may comprise a single device or multiple devices cooperating in a distributed environment. For instance, computing device 106 could be provided by multiple server devices collectively providing the functionality of computing device 106 as described herein. Additionally, other components not shown may also be included within the network environment. In some embodiments, the individual components may electronically communicate directly with each other.

Computing device 106, imaging device 108, and display device 110 may have access (e.g., via network 102) to at least one data store or repository, such as data store 104, which may include any data related to prescription data, eye refraction measurements, refraction data, user data, size data, historical data, and comparative data, as well as any associated metadata therewith. Data store 104 may further include any data related to techniques or executable instructions for obtaining refraction using a subjective refraction test process, images to present to a test subject, instructions for the test subject or eyecare practitioner, product properties, control signals, and indicator signals. In implementations of the present disclosure, data store 104 may be searchable for its data and techniques or executable instructions described herein.

Such information stored in data store 104 may be accessible to any component of system 100. The content and volume of such information are not intended to limit the scope of aspects of the present technology in any way. Further, data store 104 may be a single, independent component (as shown) or a plurality of storage devices, for instance, a database cluster, portions of which may reside in association with computing device 106, imaging device 108, display device 110, another external computing device (not shown), and/or any combination thereof. Additionally, data store 104 may include a plurality of unrelated data repositories or sources within the scope of embodiments of the present technology. Data store 104 may be local to computing device 106, imaging device 108, or display device 110. Data store 104 may be updated at any time, including information about water activity to water content conversion of various products, isotherms, measurements, historical weight, water activity, or water content data, etc.

Examples of the imaging device 108 described herein may generally implement the collection of image information. In some embodiments, the imaging device 108 may be part of the computing device 106, such as by being located within a housing of the computing device 106. In some embodiments, the computing device is a mobile computing device such as a smartphone device or tablet computer configured with a camera as the imaging device 108. In some embodiments, the imaging device 108 comprises a plurality of imaging devices capable of collecting image data. A single imaging device 108 can be used to obtain an image of the user, the user's eyes, a displayed image (e.g., on display device 110), or other objects, or multiple imaging devices can be used to obtain different images. In some embodiments, the imaging device 108 can be used to obtain user controls, commands, or other user signals. For example, the test subject may provide input to the computing device 106 using the imaging device 108 (e.g., by looking in a certain direction, by focusing on a particular target image, by speaking to the imaging device 108, etc.).

A display device 110 can be used to display images to the test subject or other user of the system 100. In some embodiments, the display device 110 can comprise an electronic display (e.g., a liquid crystal display (LCD), e-ink display, image projector, or similar device). In some cases, the display device 110 can comprise non-electronic displays such as posters, prints, books, and similar devices, and the display device is not electronically connected to the network 102. The display device 110 can be used to present a plurality of images to a test subject, such as images to evaluate the subject's refraction error in spherical, cylindrical, and axial measurements. The test subject can view the images on the display device 110 and provide input to the computing device 106 concerning their perception (e.g., sharpness or blurriness) of the images. Based on the feedback from the test subject, the display device can be made to present different images to the test subject to evaluate different aspects of their vision.

Examples herein may include computing devices, such as computing device 106 of FIG. 1. Computing device 106 may in some examples be integrated with one or more sensors (e.g., imaging device 108, microphones, keyboards, and other input devices) described herein. Computing device 106 may further be centralized, e.g., not integrated with one or more sensors described herein. In some examples, computing device 106 may be implemented using one or more computers, servers, smart phones, smart devices, or tablets. Computing device 106 may facilitate the test processes described herein. Computing device 106 may include computer readable media encoded with executable instructions (e.g., 120) and a processor 116 that may execute the instructions to provide for power system stabilization and oscillation damping control. As described herein, computing device 106 includes processor 116 and memory 118. Memory 118 may include executable instructions for weight and water content change tracking or product loss detection. In some embodiments, computing device 106 may be physically coupled to imaging device 108 and/or display device 110 (e.g., the components may be integrated and/or may be connected using a wired interface, such as bus, interconnect, board, etc.). In other embodiments, computing device 106 may not be physically coupled to imaging device 108 and/or display device 110 but collocated with the imaging device and/or the display device. In even further embodiments, computing device 106 may neither be physically coupled to imaging device 108 and/or display device 110 nor collocated with the imaging device 108 and/or display device 110. Data provided by the imaging device 108 or display device 110 may be stored in a location accessible to other components in the system in some examples.

While a imaging device 108 and display device 110 are shown in FIG. 1, any number may be used. In some embodiments, a single instrument can be used to perform the functions of these devices. Additionally, systems described herein may include multiple sensors or output devices distributed throughout the system.

Computing devices, such as computing device 106 described herein may include one or more processors, such as processor 116. Any kind and/or number of processor may be present, including one or more central processing unit(s) (CPUs), graphics processing units (GPUs), other computer processors, mobile processors, digital signal processors (DSPs), microprocessors, computer chips, and/or processing units configured to execute machine-language instructions and process data, such as executable instructions 120. A computing device 106 can also comprise other computer components (not shown) to operate and interconnect the computing device 106, such as, for example, an input/output controller, a display or other output device, input devices, network interfaces, etc.

Computing devices, such as computing device 106, described herein may further include memory 118. Any type or kind of memory may be present (e.g., read only memory (ROM), random access memory (RAM), solid state drive (SSD), and secure digital card (SD card). While a single box is depicted as memory 118, any number of memory devices may be present. The memory 118 may be in communication (e.g., electrically connected) to processor 116.

Memory 118 may store executable instructions for execution by the processor 116, such as executable instructions 120 for determining a subjective refraction of a test subject's eyes. Processor 116, being communicatively coupled to imaging device 108 and display device 110, and via the execution of executable instructions 120 for determining a subjective refraction, may track test subject input information and changes based on collected data from the imaging device 108, among other input devices.

Some embodiments relate to a software as medical device (SaMD) and mobile medical app (MMA) intended as a self-administered subjective refraction exam that measures refractive error for each of the user's eyes. Embodiments of the system may be referred to as "GoEyes" herein. The exam is a combination of several stages, each of which contains a specifically engineered image, referred to as a "target." The target may look visually different to the user according to their refraction, distances from the target, and target size. In each stage, a specific optical parameter is measured and calculated by analyzing the distance from the target, changing the target size, and what the user is actually seeing based on the user's verbal responses. Taken together, these parameters will provide the users the full details of their refraction error in terms of spherical, cylindrical, and axial measurements. Instructions, both visual and audio, will be given to guide the user through the exam. The exam is performed for each eye separately, while covering the opposite eye, so the user will need to perform the test twice.

The target user has myopia or myopia with astigmatism. The supported range of the test application (GoEyes) can be defined as follows: sphere power −1 diopter (D) to −5 D, cylinder power up to −2.5 D, and total power (sphere+ cylinder) up to −6 D. The test application may be able to identify users who are out of the testable range and terminate their test.

Clinical Principles

Systems of the present disclosure can apply the following clinical principles: Maximum distance of best acuity (MDBA) is the farthest distance from the eye in which the user can still focus the image on their retina. MDBA (in meters) correlates to the best corrective lens power (BCLP) (in diopters), such that $$MDBA(m) = \frac{-1}{BCLP[D]}.$$

Therefore, accurate distance measurement between the smartphone and the user's eye is the basis of calculating MDBA and the BCLP.

Target size on retina is identified in Log MAR units, presenting features in an angular resolution that correlates visual acuity charts. There is a minimum angle size that a user with normal vision can see at the point of focus and have the ability to resolve details in an image, such as sharp edges, different colors or hues, etc. The farther the user is from their MDBA (or in other words, "the bigger the blur"), the larger the angle size would need to be in order for them to be able to resolve details in the image. By using engineered images, or "targets," that incorporate specific details that are perceived differently when blurry versus when sharp, the user can identify the exact point in distance where the image transitions from blurry to sharp (and vice versa). That point indicates the MDBA.

Accommodation is the adjustment of the optics of the eye to keep an object in focus on the retina as its distance from the eye varies. By using MDBA (i.e., finding the farthest point of focus), mitigation of accommodation can be achieved.

Based on MDBA, target size on retina, and mitigation of accommodation, the system can use four fundamental tests/ steps to arrive at spherical, cylindrical, and axial measurements for the examined eye with the aid of the smartphone's front-facing camera and depth sensor (e.g., IPHONE® X and above or ANDROID® 6.0 and above) to measure the distance of the examined eye from the smartphone screen.

The system can implement steps including: first, displaying a dedicated target (e.g., an image) for a specific aberration. Next, mitigating accommodation. Third, locating a near point and measuring MDBA distance. Next, deducing refractive error by $$Rx = \frac{1}{MDBA}.$$

In addition to the above, in some embodiments, the user (the test subject) can be required to meet the following criteria:

(1) Have a previous glasses and/or contacts prescription within the supported range, i.e., spherical power within the range of about −1.00 D to about −5.00 D, cylindrical power up to about −2.50 D, and total power (sphere+cylinder) up to about −6.00 D;
(2) Have single vision only (no multifocal, bifocal, or progressive lenses);
(3) Have no prism measurement in their previous prescription;
(4) Have no history of amblyopia, diabetes, hypertension, glaucoma, cataracts, retinal detachment, crossed-eyes, brain injuries, neurological issues, etc.;
(5) Have no recent discomfort or symptoms of acute eye pain, flashes, and/or floaters in eyes; and
(6) Can hear, understand, and verbally respond to audio instructions.

Embodiments of the systems of the present disclosure can be downloaded and accessed without first contacting an ECP. Over the counter (OTC) use may be supported by appropriate labeling and human factors testing to verify that mitigations to identified use-related risks are sufficient. In addition, the system test results may be hidden from, inaccessible to, or otherwise not revealed to the test subject until the output has been reviewed and verified by an ECP.

An example proposed clinical workflow is as follows:
(1) User—The user can download an application of computer-executable instructions onto their smartphone or other testing-capable computing device (e.g., a computing device having an input device (e.g., camera, depth sensor, and microphone) and an output device (e.g., display device and speaker). The user will then start the application. The user will complete a questionnaire regarding their medical history and need for a glasses and/or contact lenses prescription. The purpose of the questionnaire is to identify whether the user is in the indicated user population and grant access to the refraction test. The user will follow the audio instructions provided by the application and complete the refraction test for both eyes. The user will receive a message saying the test is completed and the results are being reviewed by an eye care provider (ECP). The device can communicate/transmit the test data to the ECP.
(2) ECP—The ECP will receive a message saying that a pending test is waiting for review and their system can receive the data collected at the user device. The ECP will access a secured online environment where the test details will be presented: the user's responses to the questionnaire, test parameters, and results for spherical, cylindrical, and axial measurements. The ECP will review the test details and determine whether to approve or reject the test details.
(3) User—If the test details were approved, the user will receive their prescription along with a recommendation to check their corrected visual acuity after obtaining their glasses and/or contact lenses by taking an online visual acuity test. If the test details were rejected, the user will receive a message directing them to see an ECP in person.

Figure 2:
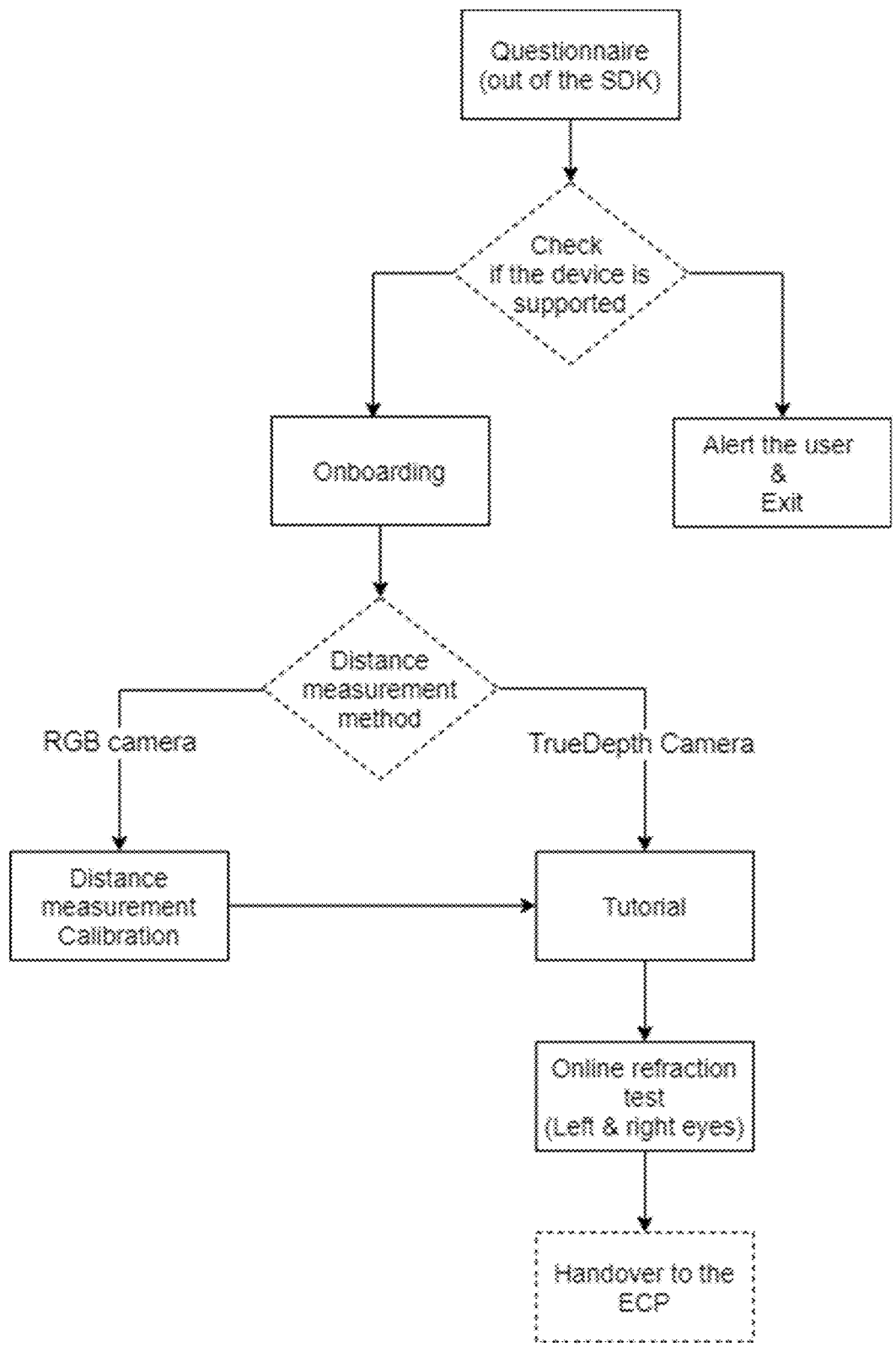
FIG. 2 illustrates a user process flow for a subjective refraction of a test subject.

An example user flow is described in FIG. 2, which can be initiated after the user has downloaded the application to their mobile device. The following sections details each action illustrated in FIG. 2. Steps, actions, and tests described in connection with FIG. 2 can be administered, skipped, or omitted, and it should be understood that sections of the process shown in FIG. 2 are optional.

Questionnaire—When the user first opens the application, the user may be prompted to complete a questionnaire before proceeding. The questionnaire may obtain the user's medical history and addresses various inclusion/exclusion requirements prior to taking the refraction test. The user inclusion requirements may be defined as including: (1) Age between 18 and 39 years old; (2) Have normal color vision; (3) Have been prescribed or use single-vision corrective eyeglasses parameters within the supported range; and (4) Can use, understand, and reply to mobile device voice instructions.

Example user exclusion requirements can be defined as including: (1) Have been prescribed or use readers, multifocal, bifocal, or progressive lenses; (2) Have prism correction in their prescription; (3) Have a history of amblyopia, diabetes, hypertension, glaucoma, cataracts, retinal detachment, crossed-eyes, brain injuries, neurological issues, etc.; or (4) Experiencing recent discomfort or symptoms of acute eye pain, flashes and/or floaters in eyes.

Check if the Device Is Supported—After the user has been identified as part of the indicated user population, the application may checks the mobile device model and will accept devices having prerequisite hardware and software configurations (e.g., IPHONE X and above with iOS 13.0 and above and ANDROID models according to a whitelist with OS ANDROID 6.0 MARSHMALLOW and above). Automatic alerts may alert the user if the mobile device is not supported or certain sensors (e.g., the gyro sensor) are not responding.

The application can use at least two methods for distance measurements. First, a distance or depth sensor (e.g., a TRUEDEPTH® sensor or infrared dot projector) which does not require calibration, but it is not available in all mobile devices, or second, an RGB camera method (e.g., if dedicated depth sensors are not available).

Onboarding—If the mobile device is supported, the user can be directed through an onboarding step. Onboarding may include the following steps: (1) Presenting the "About Product" page which introduces the users to the application, (2) presenting a user agreement to application privacy notice and terms and conditions, and (3) requesting access to required phone features (e.g., camera, microphone, and speech recognition). Onboarding can also comprise providing guidance to users regarding test environment requirements.

Figure 3:
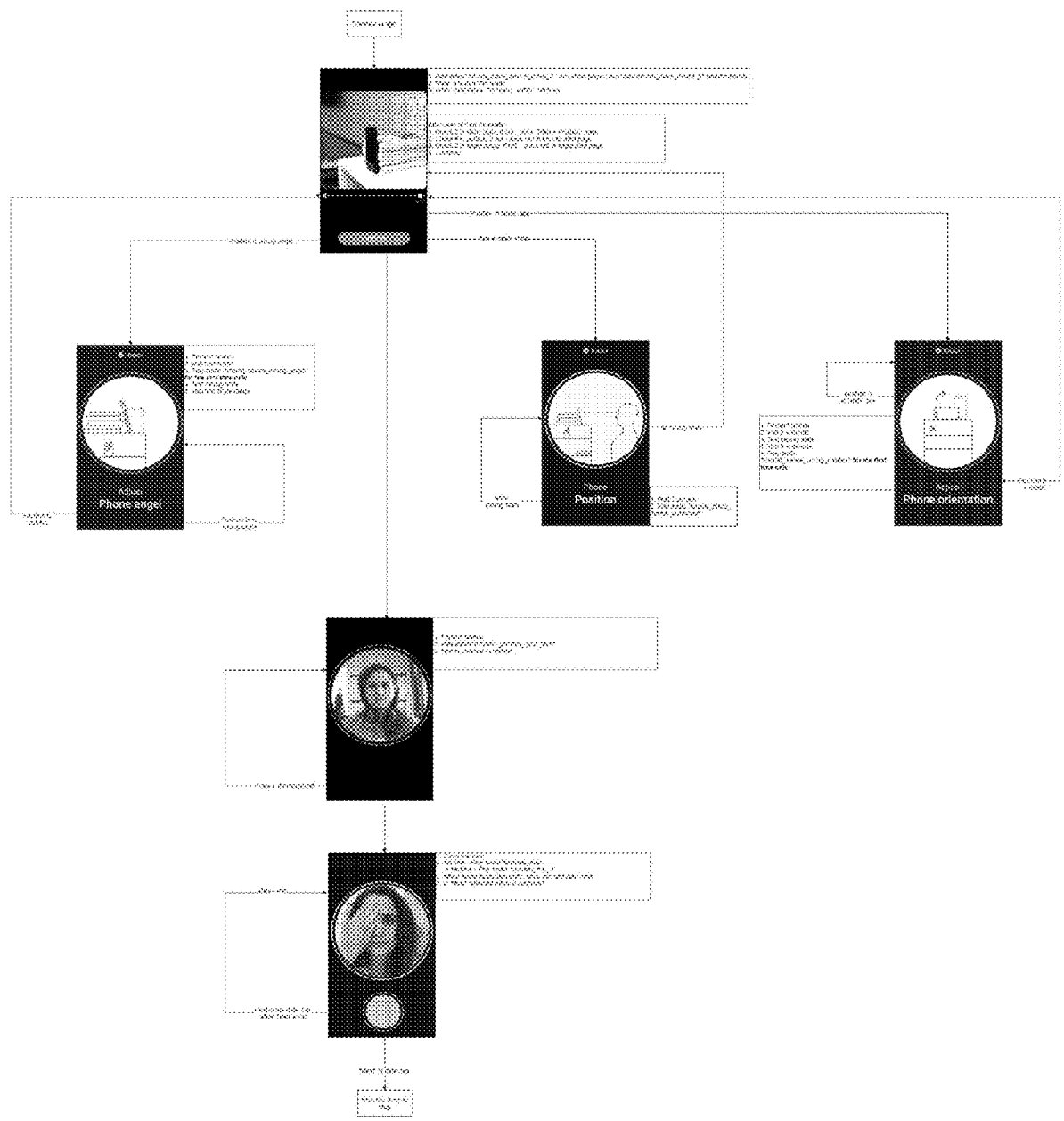
FIG. 3 shows an interactive process flow for setting up a test environment for an online refraction test.

Tutorial—Next, the users can be directed through a tutorial step. The tutorial (schematically shown in FIG. 3) can be an interactive flow where the user will set up the test environment conditions for the online refraction test. Steps in the tutorial can include operations to: (1) Guide the user how to place the device; (2) Ensure the device is placed in a steady state; (3) Ensure the device is placed in portrait position; (4) Ensure the device is placed in the correct angle; (5) Ensure the user's face is detected; (6) Guide the user to remove their glasses and cover the left eye; and (7) Ensure the user understands how to use the audio communication.

Figure 4:
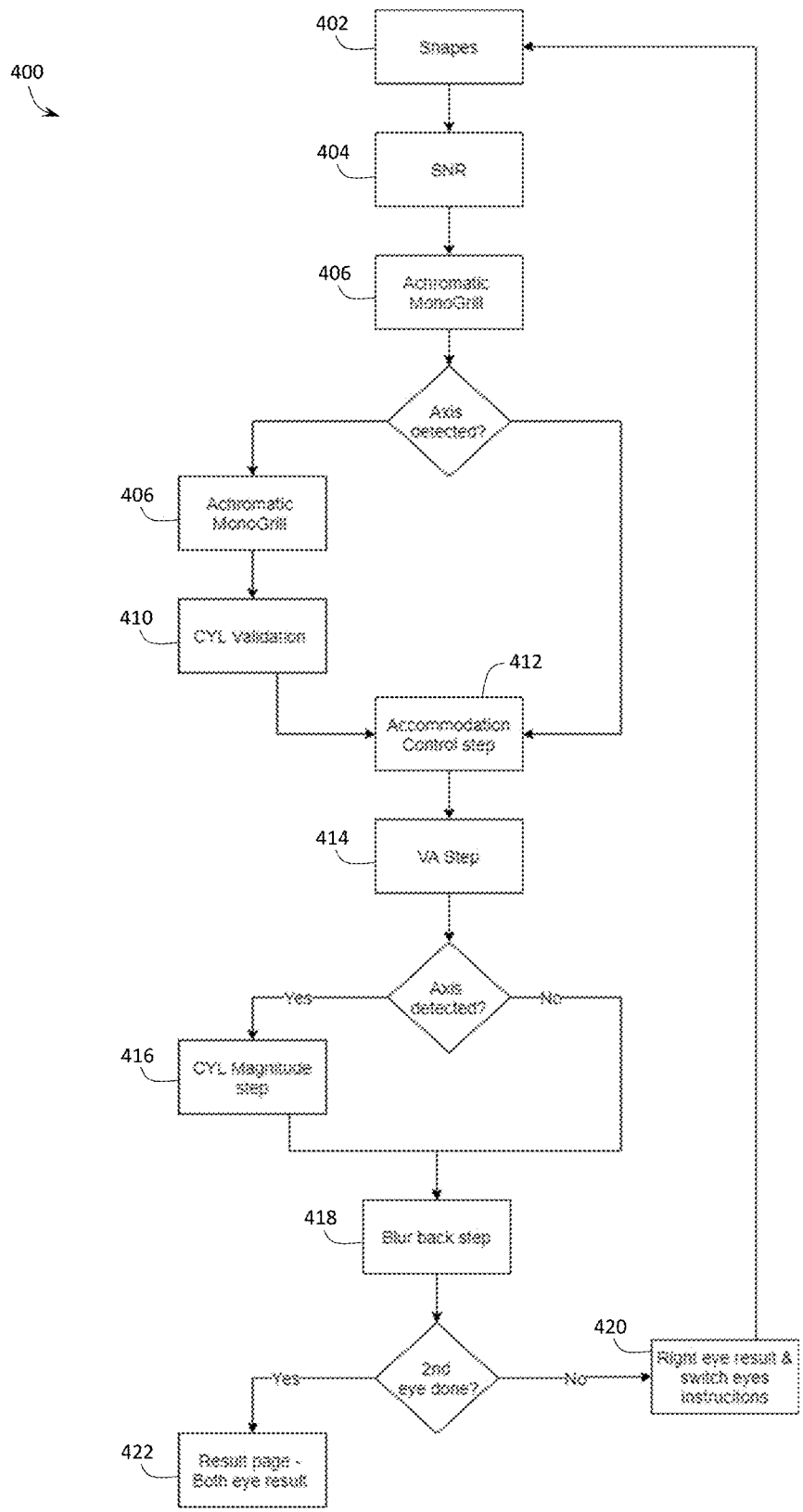
FIG. 4 shows a process flow for a refraction test.

Refraction Test (Left and Right Eyes)—The refraction test 400 can be conducted for each eye separately, starting, for example, with the user's right eye, as shown in FIG. 4, then switching to the left eye.

Shapes—The shapes step (i.e., the shapes test 402) can include actions to screen out high myopic, emmetropic, and hyperopic users that should be excluded from the test (i.e., <−5 D and >−1 D); and to locate the approximate sphere of the measured eye.

Targets in the shapes test can be configured and designed to emphasize spatial isotropic features while the target is within the distance corresponding sphere equivalent refractive error. As the target is further than the sphere distance, the target can vanish (i.e., the target's blurred features are perceived to blend into the background). The shapes can "appear" to the test subject immediately when the user reaches a distance where the image first lands on the retina, thus obtaining an MDBA for the equivalent sphere power.

Figure 5:
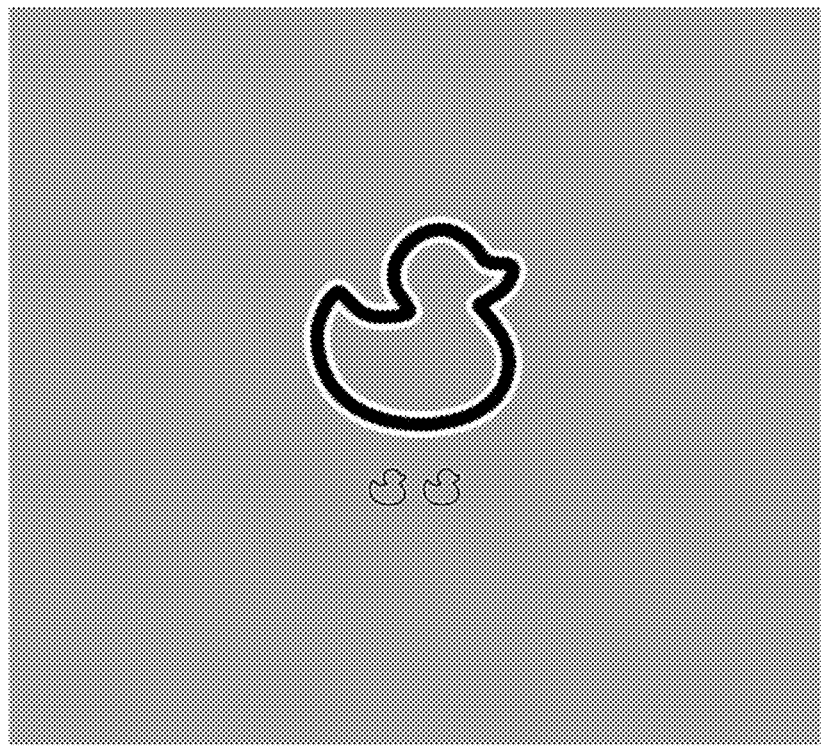
FIG. 5 shows a target for a screening.
Figure 6:
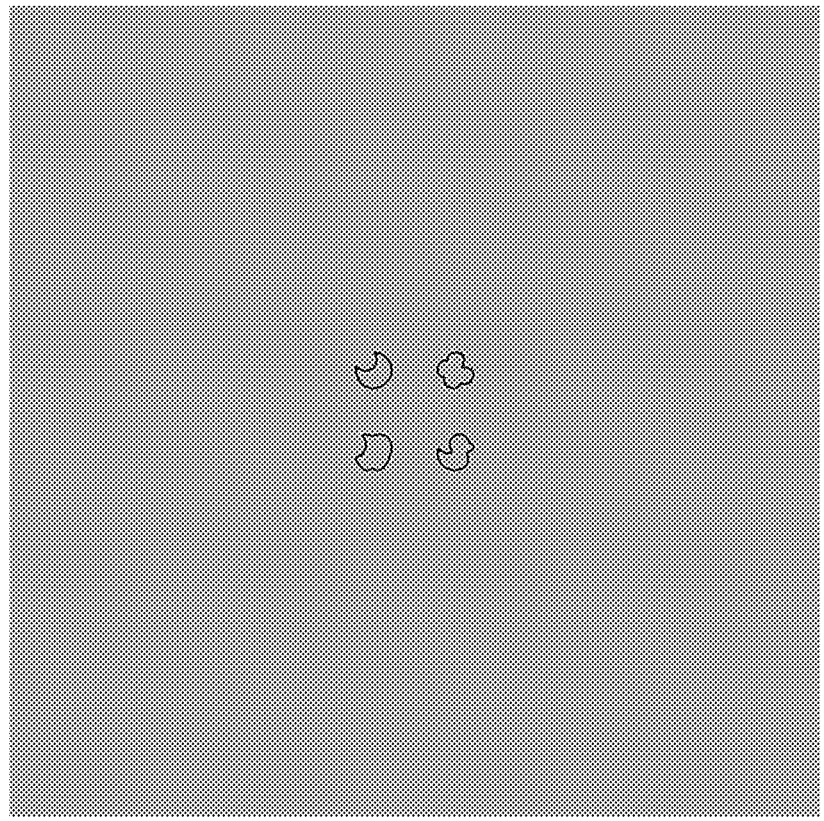
FIG. 6 shows a target for locating an approximate sphere.

The target for screening can include one large shape (e.g., a duck) and two small shapes (e.g., small ducks, as shown in FIG. 5), and the target for the locating the approximate sphere consists of a combination of the first shape and a set of other shapes (FIG. 6). The number of the first shape and the additional shapes (and their order) can be shown in a randomized pattern.

An example of a shapes test is depicted in FIG. 7 for a user whose right eye has a sphere of −3 D, cylinder of −0.5 D, and axis of 135 degrees. The shapes test can differ depending on the user's responses to the prompts provided by the app, such as by repeating steps, changing the images shown, waiting for the test subject, etc.

Spokes and Rings (SNR)—The spokes and rings (SNR) test 404 can include: (1) Identifying if a user has an astigmatism, (2) Measuring the cylinder axis, if astigmatism exists, and (3) Measuring sphere power by obtaining the MBDA of the features at a specified meridian.

If there is an asymmetric optical aberration, such as astigmatism, the perceived SNR image (e.g., the target shown in FIG. 8) may appear deformed to the test subject according to the astigmatic aberration. When the phone is located close to the sphere distance, the spatial features aligned along the axis of the astigmatism "fall" on the retina and are thus perceived as dark and sharp lines, while the perpendicular features are focused anterior to the retina, thus perceived gray and blurry.

Once a certain axis is identified where some lines are darker than others (astigmatism case) or in the case of no astigmatism (spherical) where all the lines are perceived symmetrically, the user can provide feedback by grading the perceived sharpness and darkness of the lines at farther distances on a numerical scale. Identifying the farthest distance of perceived sharpness, beyond which the lines appear to blur, is used to determine the MDBA of the sphere power.

Figure 8:
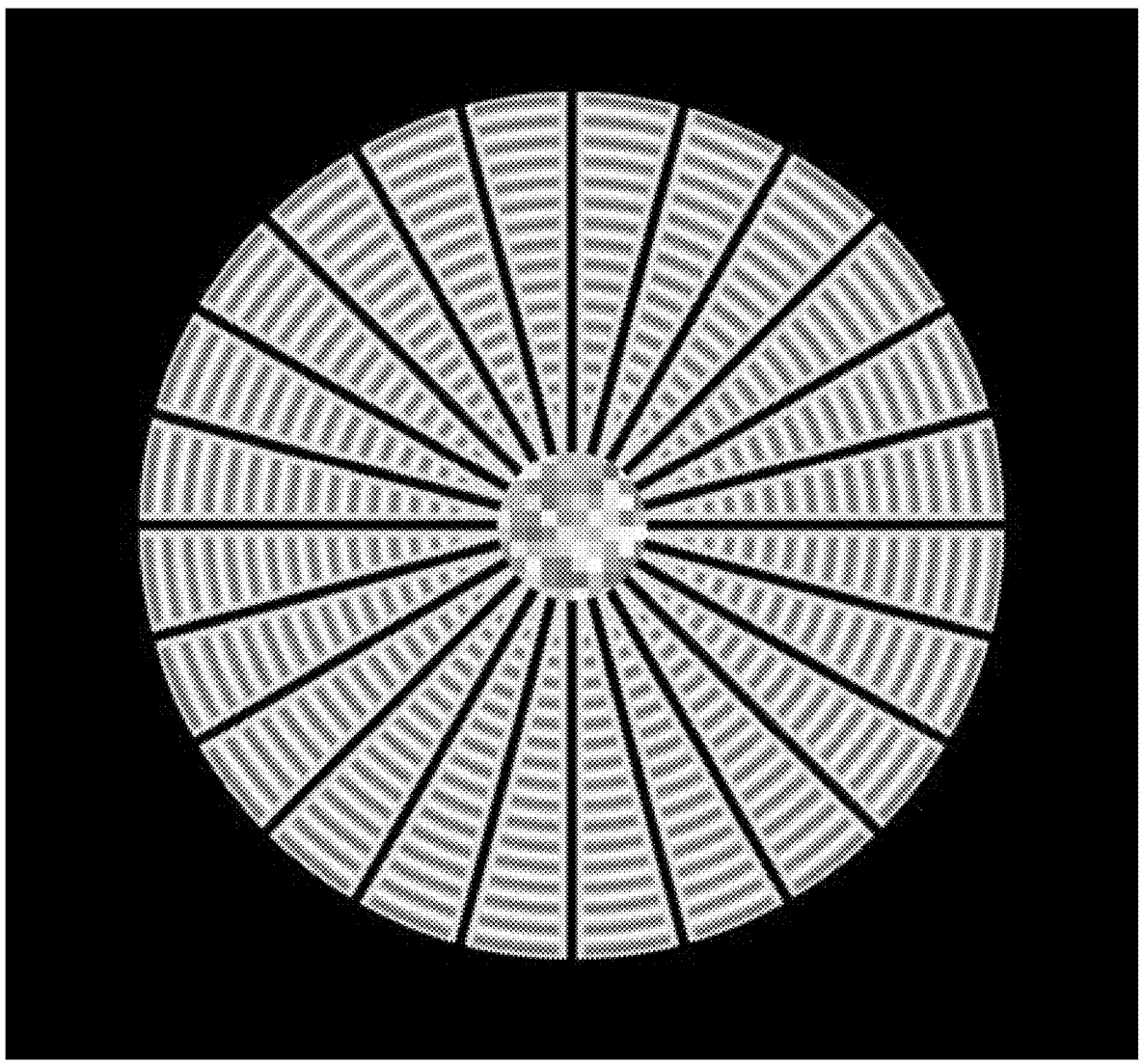
FIG. 8 shows a target for a spokes and rings test.

An example SNR target is shown in FIG. 8. The "spokes" can be labeled with different colors to help the users identify which lines appear darkest or "blackest" and how sharp those lines are on a numerical scale, as indicated in FIGS. 9A-9B.

An example of the SNR test is depicted in FIGS. 9A-9B for a user whose right eye has a sphere of −3 D, cylinder of −0.5 D, and axis of 135 degrees. The SNR test differs depending on the user's responses to the prompts provided by the app, such as by repeating steps, changing the images shown, waiting for the test subject, etc.

Figure 10:
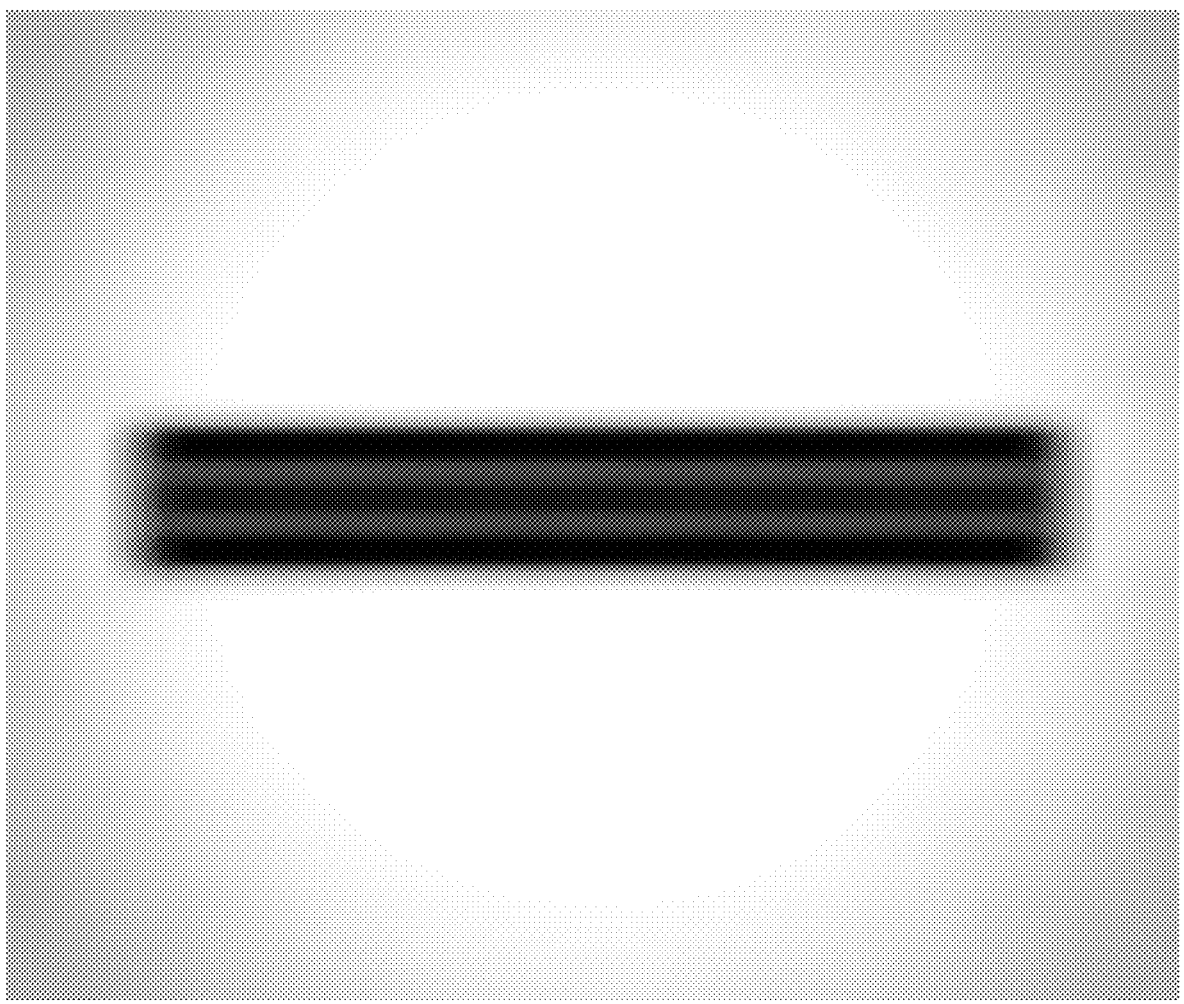
FIG. 10 shows an achromatic monogrill target.

Achromatic MonoGrill—The achromatic monogrill test 406 can fine tune the eye's sphere power measurement and, for astigmatism, obtains cylinder power measurement. An example achromatic monogrill target is depicted in FIG. 10. The target is designed to blend the two parallel middle bright lines into the dark rectangular background bar when a slight blur is introduced, and therefore has a binary perception by the test subject (i.e., they only see or don't see the target). The target has one-dimensional features (i.e., lines) and can be rotated to the tested meridian; thus, the responses are related to the power of a specific rotated meridian being tested (e.g., a meridian identified in connection with the SNR test). This allows the system to obtain the test subject's MDBA by having the user pull back (i.e., move away from the display image) until the middle light lines are no longer apparent and provide feedback at those distances. Displaying the target at several frequencies (i.e., display refresh rates) is used to identify the optical transfer function and to obtain the spherical and near powers accordingly.

An example of the achromatic monogrill test is depicted in FIGS. 11A-11G for a user whose right eye has a sphere of −3 D, cylinder of −0.5 D, and axis of 135 degrees. The achromatic monogrill test can differ depending on the user's responses to the prompts provided by the testing system, such as by repeating steps, changing the images shown, waiting for the test subject, etc.

Figure 12:
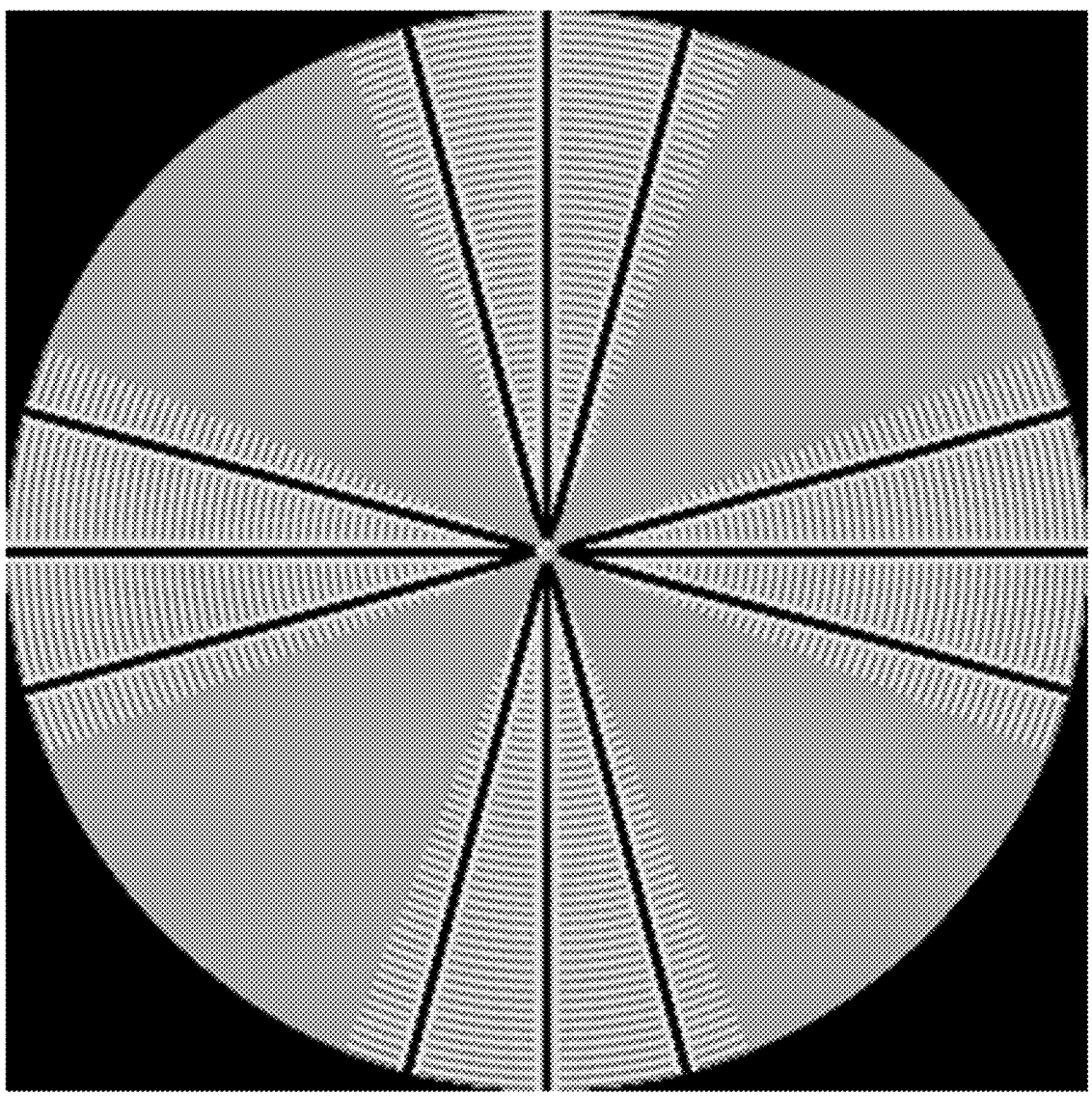
FIG. 12 shows a cylinder validation target.

Cylinder (CYL) Validation—The cylinder (CYL) validation test 410 can refine the axis measurement and derive a near power measurement using an MDBA approach by processing the sharpness score vector for the cylinder meridian. An example CYL validation target is shown in FIG. 12. Observation of the effect of the astigmatism angle of the presented features is optimal when viewed at the distance of the sphere. Once the sphere power is obtained (e.g., using the achromatic monogrill target of FIG. 10 and described above), the axis measurement is repeated at the sphere distance (as opposed to the approximate sphere equivalent distance). Furthermore, to increase the resolution of the axis measurement, the system may use a super resolution procedure with a low-resolution target. In other words, the target, with a specified basic angle feature, such as the angle created by two adjacent spokes, can be rotated half of that base angle. Then, the two (or more) measurements can be averaged.

Obtaining the MDBA for features presented at the cylinder meridian corresponds to the near power. Positioning the phone close to the approximate near power (obtained in previous steps) and inquiring about the sharpness perceived by the user for features that co-align with the cylinder axis provide a quantitative measure for the MDBA function around the near power.

An example of the CYL validation test is depicted in FIG. 13 for a user whose right eye has a sphere of −3 D, cylinder of −0.5 D, and axis of 135 degrees. The CYL validation test can differ depending on the user's responses to the prompts provided by the app, such as by repeating steps, changing the images shown, waiting for the test subject, etc.

Axis Refinement—The axis refinement test can refine the axis measurement by receiving feedback upon the darkest lines while the target itself is rotated in finer angles than the angles between two adjacent spokes. An example target used for the axis refinement test can be the same as the target used for the SNR test (i.e., FIG. 8).

An example of the axis refinement test is depicted in FIG. 14 for a user whose right eye has a sphere of −3 D, cylinder of 1.5 D, and axis of 5 degrees. The axis refinement test differs depending on the user's responses to the prompts provided by the application, such as by repeating steps, changing the images shown, waiting for the test subject, etc.

Accommodation Control—The accommodation control test 412 can validate the sphere power under an accommodation relaxation procedure. Having the user open both eyes allows the eyes to reach a minimum accommodative state. The target used for the accommodation control test can be the same as the target used for the achromatic monogrill test (e.g., FIG. 10). The system can require quick responses (e.g., within about 2-3 seconds) to the target after the tested eye is covered again. In such a short period of time, unwanted accommodation does not kick in yet, and therefore, the eye is tested in an essentially or completely accommodation-free state.

An example of the accommodation control test is depicted in FIGS. 15A-15B for a user whose right eye has a sphere of −3 D, cylinder of −0.5 D, and axis of 135 degrees. The accommodation control test can differ depending on the user's responses to the prompts provided by the app, such as by repeating steps, changing the images shown, waiting for the test subject, etc.

Visual Acuity (VA)—The visual acuity (VA) test 414 can validate that the best corrected visual acuity (BCVA) under the determined refraction error is 20/25 or better. The target used for the VA test is the same as the target used for the achromatic monogrill test (e.g., FIG. 10). The target shown can presents two light lines separated by 6 arcmin. The size of early treatment diabetic retinopathy study (ETDRS) 20/20 letter is 5 arcmin with each bar 1 arcmin. Low-contrast lines with high-contrast background bridge the resolution gap. Obtaining the visual acuity at different meridians without cylinder lenses is utilized by aligning a one-dimensional target with the tested meridian.

An example of the VA test is depicted in FIG. 16 for a user whose right eye has a sphere of −3 D, cylinder of −0.5 D, and axis of 135 degrees. The VA test can differ depending on the user's responses to the prompts provided by the app, such as by repeating steps, changing the images shown, waiting for the test subject, etc.

Figure 17:
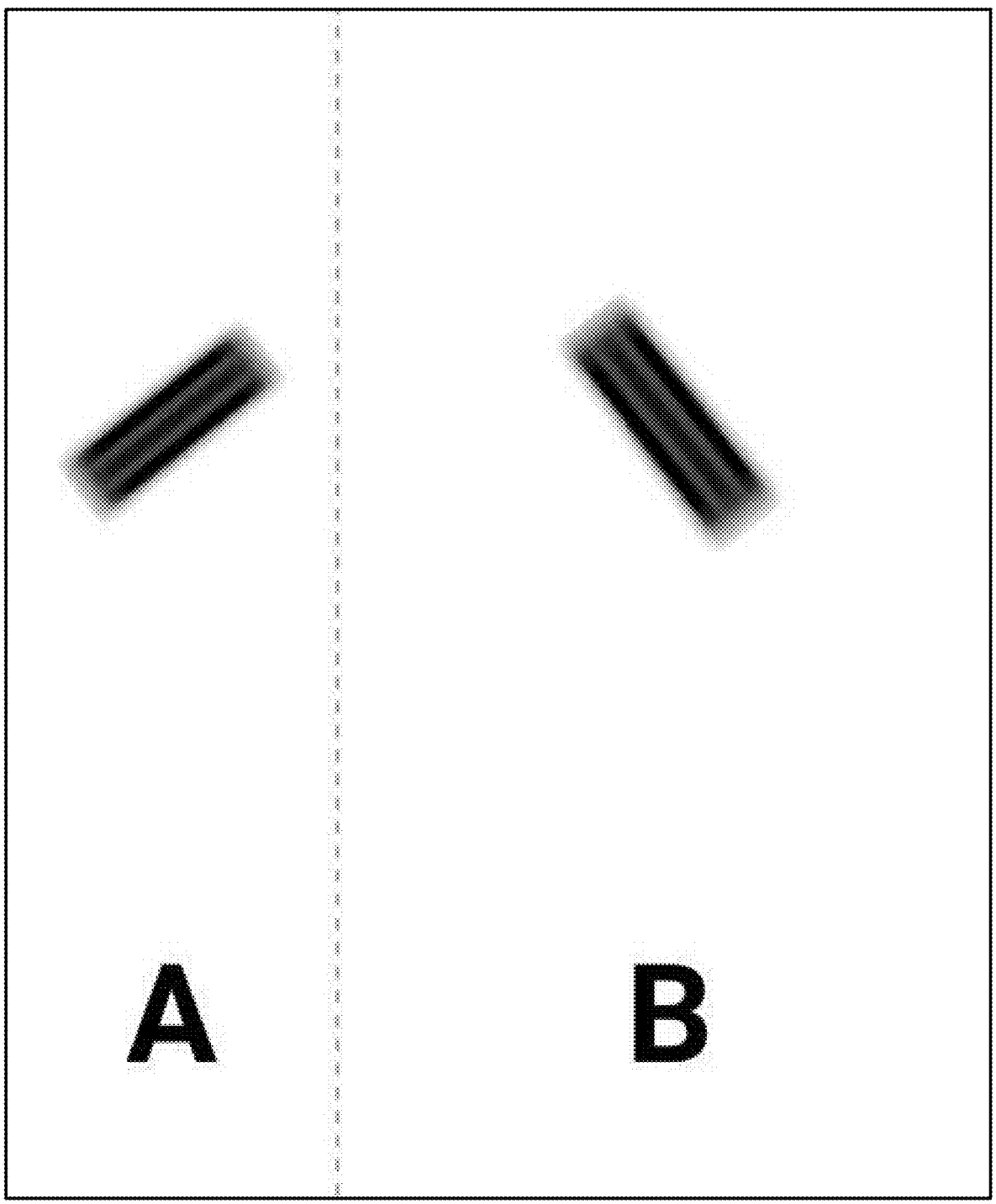
FIG. 17 shows an example group of steps for a cylinder magnitude test.

Cylinder (CYL) Magnitude—The cylinder (CYL) magnitude test 416 can validate cylinder power while mitigating any temporal changes of the accommodative state. In addition, the CYL magnitude test derives under sphere power measurement. An example target used for the CYL magnitude test is shown in FIG. 17, which includes a pair of dark bars oriented at different angles relative to each other, and each dark bar having a respective pair of light parallel lines extending through them. A dashed line separates the dark bars into left and right sides of the target image, and two indicators (e.g., letters) designate different sides of the dashed line. As the primary cylinder power measurements are derived from sphere power and near power conducted at two different points in time, a change of the accommodative state in between may affect the calculated cylinder power. To mitigate this, the user may be positioned at their sphere power distance where the threshold of required resolution per the major meridian (i.e., sphere meridian) is reached. The system can then guide the user to identify a Log MAR delta and a distance at which the user shifts from a position where they can identify both meridians to an about +0.25 D position where both meridians can no longer be identified. The system can then validate the cylinder power from the delta between the meridian targets.

An example of the CYL magnitude test is depicted in FIGS. 18A-18B for a user whose right eye has a sphere of −3 D, cylinder of −0.5 D, and axis of 135 degrees. The CYL magnitude test can differ depending on the user's responses to the prompts provided by the app, such as by repeating steps, changing the images shown, waiting for the test subject, etc.

Blur Back—The blur back test 418 determines the final MDBA while mitigating the accommodation. The system can set the distance of user at an about +0.75 D blur from the final sphere and can confirm that the user cannot achieve better resolution than 0.55 Log MAR using the achromatic monogrill target (e.g., FIG. 10). The system can employ accommodation relaxing methods that push the user to a more distant location from the display screen while maintaining the same best corrected acuity. This is derived from the methodology used in optometry to mitigate the accommodation by placing +1.00 D lenses over the test subject's obtained prescription and to validate that the acuity has deteriorated as expected by +1.00 D lens. While at this myopic shift any excessive accommodation will only provide a poorer vision, the user is likely to release accommodation. Similarly, the system can push the user farther from the obtained sphere or near powers, creating the same +1.00 D in vergence.

"Rest Your Eyes"—Throughout the process flow of FIG. 4 and between the tests/steps in the flow, the app guides the user to relax their eyes by looking as far as possible (e.g., to the horizon, out the window, etc.).

Second Eye Flow—At the end of the first eye flow (e.g., the right eye has been tested), the system can instruct the user to cover the other eye (e.g., the left eye) and provide input (e.g., click) to continue. The second eye testing flow (e.g., starting at block 420) can omit training blocks and can include short versions of the audio instructions provided previously while the first eye flow was being followed.

Results—After both eyes are evaluated with the refraction test, the user can be provided a message 422 saying the test is completed and that results were electronically sent to an ECP. The ECP can use these results and the questionnaire data as part of their comprehensive diagnostic process. The user may not be able to view their results in the app until the ECP verifies the results and writes the prescription for glasses and/or contact lenses.

Overview of Device Development

Figure 19:
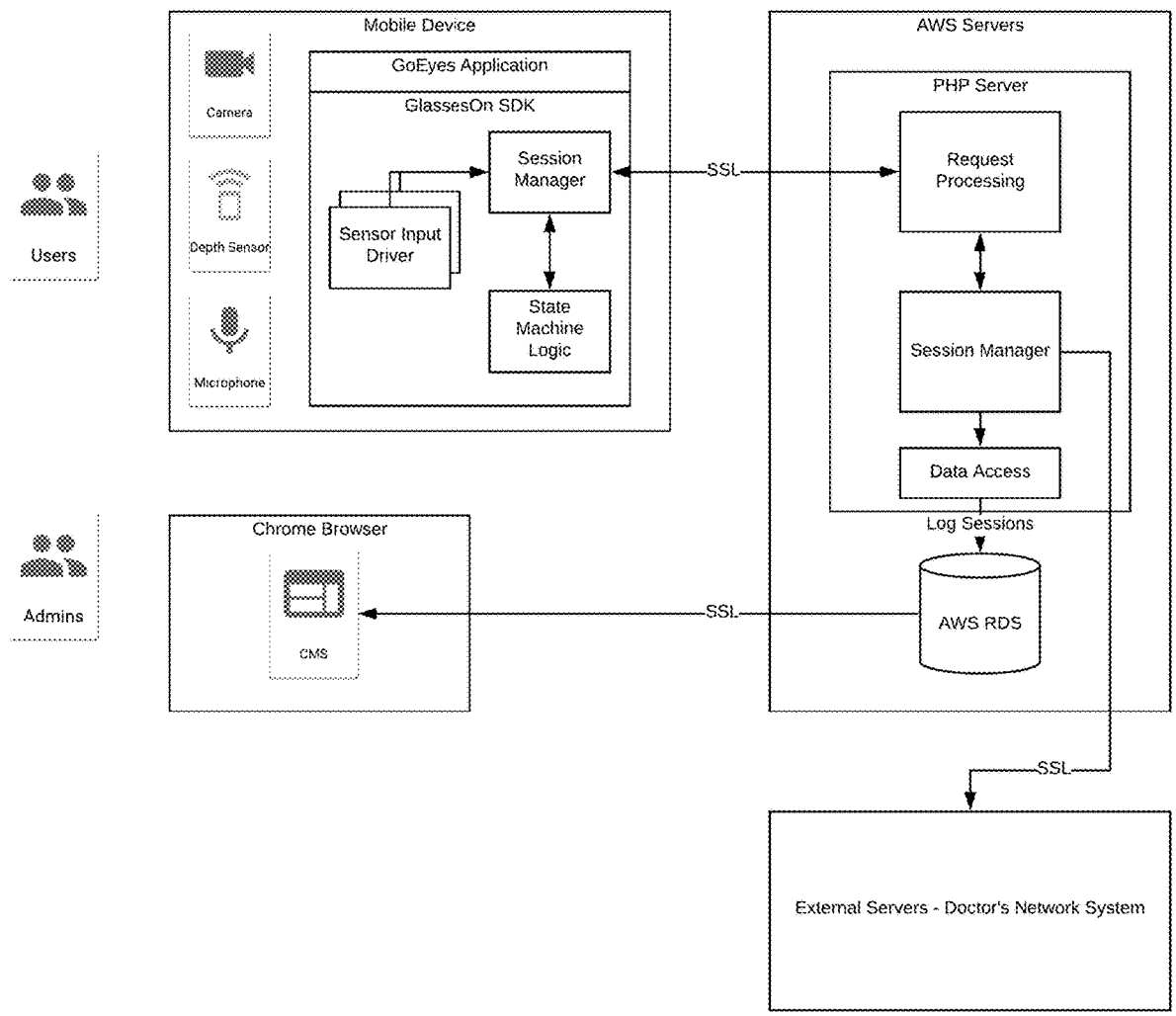
FIG. 19 shows a software system block diagram.

FIG. 19 illustrates an example software system block diagram. The system is composed of a mobile device application, cloud servers and a SPA (Single Page Application) web client. The system can be designed to support various operating systems and devices, such as, for example, both IOS- and ANDROID-based mobile devices (under a whitelist of supported devices).

Each of the following components can run separately in a different environment: the IOS/ANDROID application, a PHP Server running on a server (e.g., an AWS server), a CMS (Admin Client) running on a browser (e.g., a CHROME® browser (downloaded from the server))

The system can be designed around a classical client-server design. The clients present the data to the user and receives user inputs, and the server gets the requests from the client, prepares the data, and sends it back to the client. The system uses "Thin Client" design wherever possible. Principal system logic is found only in the server. Only mandatory real-time logic is computed on the client.

The system's client can be divided into an SDK (Software Development Kit) responsible for all the testing application's screens and logic, and an application serving a container running the SDK.

The testing application and related system can include various software modules.

Client Mobile GlassesOnSDK—This module can be configured as a wrapper for all the testing application's client code. All of the logic, sensor input, and server connectivity are done in this high-level module. This module can also wrap other products' client code. The API of this module can be used to integrate the testing application's functionality in third party applications.

Client Mobile GoEyes Application—This module can be configured as a container running only the Client Mobile GlassesOnSDK and can provide the ability to test, deploy, and distribute the SDK's functionality inside the application.

Client Session Manager Module—This module can be configured to be responsible for all the client's side logic in the testing application's exam. The logic for some of the testing application's exam process needs to be computed in real-time. This logic can be written in/including in this module. The module's definition and parameters can be received from the Server Session Manager Module Flows and Pages sub-modules. The module can receive or obtain the parameters from the server (the data from the Sensor Input Modules and the decision from the Client State Machine Logic Module) and decide what to present to the customer in the client application. This module can be used as a connectivity bridge between the client and the server.

Client State Machine Logic Module—This can be a sub-module of the Client Session Manager Module. This module can be specifically designed to hold the client-side logic of deciding what to present to the user in relation to the input data from the sensors and the current state in the flow. This client logic can be in real-time, so it cannot use the Server Session Manager Module.

Client Sensor Input Modules (Services)—This module can be configured as a wrapper for all the sensors services sub-modules on the client. Each service gets the raw data from the sensor and runs relevant calculations on the data and provides the results to the Client Session Manager Module. Some services are running neural networks on the data received from the sensors, e.g., using a CORE ML (IOS)/TENSORFLOWLITE (ANDROID) framework.

Server Session Manager—GoEyes Server Logic Module—This module can be responsible for all the logic in the testing application's exam. The logic can be divided into flows. Each flow is a definition of a state machine of pages seen by the customer. The flow can define the order of the pages. Each page sub-module is the definition of what is seen by the customer and all the inner logic of this specific page (i.e., screen). This module can provide the client with all the information needed to decide what the next page is to be presented in the client and all the parameters of how to show the page and its inner behavior.

Server Request Processing Module—This is a general module wrapping the server functionality supporting the main logic module—GoEyes Server Logic Module. This module provides networking, security, logging, and server routing.

Server Data Access Module—This is a general module responsible for saving the reading data from the database. This module holds the needed schema information and saves all the testing application's sessions when used by the GoEyes Server Logic Module.

Administration CMS SPA Module—This module is the main administration console of the system. The module is a single page application built in a language such as JAVASCRIPT®. This module can provide the ability to review all of test application sessions data.

Figure 20:
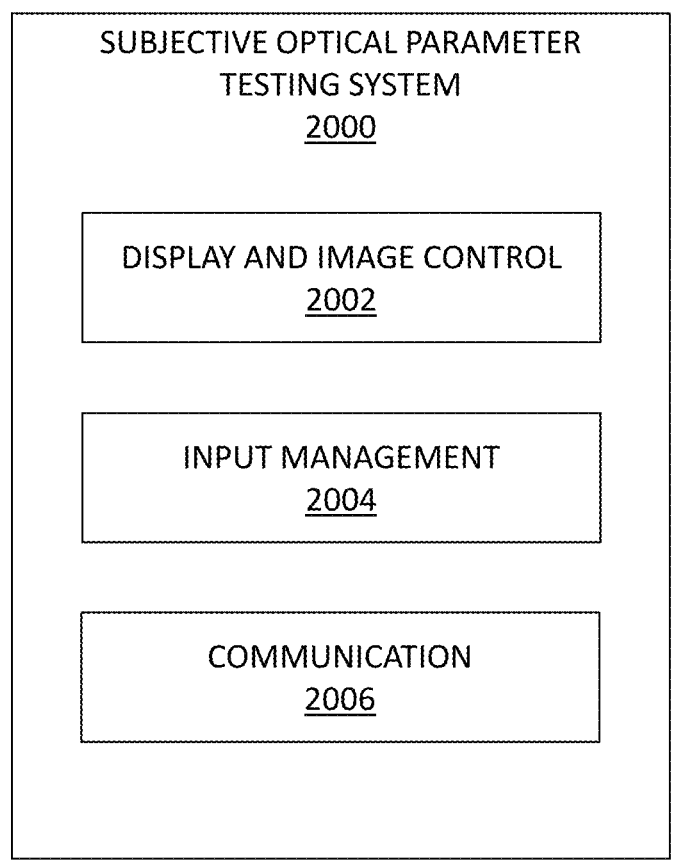
FIG. 20 shows a functional diagram of a subjective optical parameter testing system.

FIG. 20 depicts a functional diagram of a subjective optical parameter testing system 2000. The system 2000 can include a collection of functional modules that cooperate to carry out techniques described herein. For example, the system 2000 can broadly be configured to request, receive, analyze, and process subjective vision indications from a test subject to determine optical parameters of an eye of the test subject.

To do so, the system 2000 can include a display and image control module 2002. The display and image control module 2002 can be configured to display at least one image to a test subject. The image(s) displayed can include any of the images referenced above for various testing procedures and steps, including, for example, any of the steps, tests, and procedures shown and described in connection with FIG. 4 and the related steps, tests, and procedures described in connection with FIGS. 5-18B. The display and image control module 2002 can therefore select an image to display to the test subject based on an optical parameter currently being tested (e.g., an image for testing accommodation control, spokes and rings, etc.), display the selected image to the test subject (e.g., via an electronic display like display device 110), and can display instructions to the test subject (e.g., instructions to change their position relative to the image/display, instructions to cover an eye, and other instructions described above). As a result, the display and image control module 2002 can guide the test subject through a test (or a set of tests (e.g., sequentially)) to determine an optical parameter of the eye of the test subject.

In some embodiments, an input management module 2004 can be included to obtain and receive input from the test subject. The input can be a "subjective" input, meaning the input is based on the test subject's perception of a portion of the test (e.g., the test subject's provided indication of visual clarity or their ability to see or read certain shapes or objects in the images being provided and displayed to the test subject), as opposed to an objective input, such as a measurement of the eye of the test subject using an external tool. The input management module 2004 can control and receive signals from an input device such as, for example, an input device connected to the computing device 106. In some embodiments, the input device can comprise a microphone, keyboard, mouse, or other computer interface configured to convert user inputs into computer-readable signals. In some embodiments, an input device can include a camera, and the input management module 2004 can execute shape-detection, text-detection, or other computer vision techniques to detect user input (e.g., a thumbs up or "okay" hand sign from the test subject).

The display and image control module 2002 and input management module 2004 can operate together to provide and receive input from the test subject during a testing procedure. For example, the display and image control module 2002 can display a set of shapes to the test subject while the input management module 2004 obtains input indicating the sphere of the eye of the test subject. Similarly, the display and image control module 2002 can display a set of spokes and rings, an accommodation control image, or a visual acuity test image, and the input management module 2004 can obtain input indicating a cylinder measurement of the eye, input validating the sphere of the eye, or a best corrected visual acuity (BCVA) of the eye, respectively.

In some embodiments, the display and image control module 2002 can output images such as shapes having different appearance characteristics, such as images that are smaller or larger (e.g., as described in connection with FIGS. 5-6 and elsewhere herein), rotated, etc. Accordingly, the images displayed and inputs received can change as a series of tests are conducted over time to detect subjective aspects of the test subject's vision.

The system 2000 can also include a communication module 2006 configured to generate a signal providing information about the collected input from the test subject. For example, the communication module 2006 can be configured to interface with an external device (e.g., data store 104 or servers or administrators disclosed in connection with FIG. 19). The communication module 2006 can therefore be used to transmit information about the test subject, the tests performed, determined optical parameters of the eye, and related information disclosed herein.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising".

What is claimed is:

1. A method comprising:
    displaying at least one image to a test subject, wherein the at least one image has at least one one-dimensional feature having a visual appearance to the test subject based on physical characteristics of an eye of the test subject;
    obtaining input from the test subject regarding the visual appearance of the at least one image at a plurality of distances between the eye and the at least one image, wherein the input includes a binary perception by the test subject of the at least one image at the plurality of distances, wherein the binary perception includes an indication of whether the test subject sees or does not see the at least one one-dimensional feature; and
    transmitting the input from the test subject.

2. The method of claim 1, wherein displaying the at least one image to the test subject and obtaining input from the test subject includes:
    displaying a set of shapes to the test subject and obtaining input indicating sphere of the eye;
    displaying a set of spokes and rings to the test subject and obtaining input indicating a cylinder measurement of the eye;
    displaying an accommodation control image to the test subject and obtaining input validating the sphere of the eye;
    displaying a visual acuity test image and obtaining input indicating a best corrected visual acuity (BCVA) of the eye; and
    providing instructions to relax the eye.

3. The method of claim 1, wherein displaying the at least one image includes displaying the at least one image at a first size and displaying the at least one image at a second size.

4. The method of claim 3, wherein the at least one image is simultaneously displayed at the first and second sizes.

5. The method of claim 3, wherein the at least one image is sequentially displayed at the first and second sizes.

6. The method of claim 1, wherein the input is a subjective input based on the physical characteristics of the eye of the test subject.

7. The method of claim 1, wherein the input from the test subject includes an indication of a brightness value of a portion of the at least one image.

8. The method of claim 1, further comprising providing instructions to the test subject to change a length of an optical path between the test subject at the at least one image.

9. The method of claim 1, wherein the input from the test subject includes an indication of sharpness of a portion of the at least one image.

10. A product comprising one or more tangible computer-readable, non-transitory storage media comprising computer-executable instructions operable to, when executed by at least one computer processor, enable the at least one computer processor to cause a computing device to:
    display at least one image to a test subject, wherein the at least one image has at least one one-dimensional feature having a visual appearance to the test subject based on physical characteristics of an eye of the test subject;
    obtain input from the test subject regarding the visual appearance of the at least one image at a plurality of distances between the eye and the at least one image, wherein the input includes a binary perception by the test subject of the at least one image at the plurality of distances, wherein the binary perception includes an indication of whether the test subject sees or does not see the at least one one-dimensional feature; and
    transmit the input from the test subject.

11. The product of claim 10, wherein displaying the at least one image includes displaying the at least one image at a first size and displaying the at least one image at a second size.

12. The product of claim 10, wherein the instructions are further operable to enable the at least one computer processor to cause the computing device to provide instructions to the test subject to change a length of an optical path between the test subject and the at least one image.

13. The product of claim 10, wherein the visual appearance of the at least one image includes a brightness or sharpness of a portion of the at least one image.

14. An apparatus for subjectively testing an optical parameter of an eye of a test subject, the apparatus comprising:
    a processor;
    a display;
    an input device;
    a network device; and
    a memory device including executable instructions operable, when executed by the processor, to:
        display at least one image to a test subject via the display, wherein the at least one image has at least one one-dimensional feature having a visual appearance to the test subject based on physical characteristics of an eye of the test subject;
        obtain input from the test subject via the input device regarding the visual appearance of the at least one image at a plurality of distances between the eye and the at least one image, wherein the input includes a binary perception by the test subject of the at least one image at the plurality of distances, wherein the binary perception includes an indication of whether the test subject sees or does not see the at least one one-dimensional feature; and
        transmit the input from the test subject via the network device.

15. The apparatus of claim 14, wherein displaying the at least one image includes displaying the at least one image at a first size and displaying the at least one image at a second size.

16. The apparatus of claim 14, wherein the instructions are further operable to enable the processor to provide instructions to the test subject to change a length of an optical path between the test subject and the at least one image.

17. The apparatus of claim 14, wherein the visual appearance of the at least one image includes a brightness or sharpness of a portion of the at least one image.

* * * * *